United States Patent [19]

Fleury

[11] 3,980,946
[45] Sept. 14, 1976

[54] APPARATUS FOR MEASURING THE ELECTRICAL CONDUCTIVITY OF A LIQUID,

[75] Inventor: Jacques Fleury, Paris, France

[73] Assignee: Societe Anonyme Automobiles Citroen, Paris, France

[22] Filed: Apr. 4, 1975

[21] Appl. No.: 565,112

[30] Foreign Application Priority Data
Apr. 5, 1974 France .............. 74.12699

[52] U.S. Cl. .............. 324/30 A; 204/244; 324/30 B
[51] Int. Cl.² ........................... G01N 27/42
[58] Field of Search .......... 204/244; 324/30 A, 30 B

[56] References Cited
UNITED STATES PATENTS 2,607,223 8/1952 Fleming .......................... 324/30 A
3,387,209 6/1968 Eames et al. .................. 324/30 A
3,396,331 8/1968 Sperry .......................... 324/30 A Primary Examiner—R. V. Rolinec
Assistant Examiner—Michael J. Tokar
Attorney, Agent, or Firm—Karl F. Ross; Herbert Dubno

[57] ABSTRACT

In apparatus for measuring the electrical resistance of a liquid employing two parallel channels for the liquid, a single induction coil is located at one of the points of connection of the channels and a single measuring coil at the other of said points of connection. In this way, parasitic electric circuits in the liquid and mutual interaction between the coils are avoided. The coils are preferably arranged coaxially above respective circular passages connecting the parallel channels.

4 Claims, 4 Drawing Figures

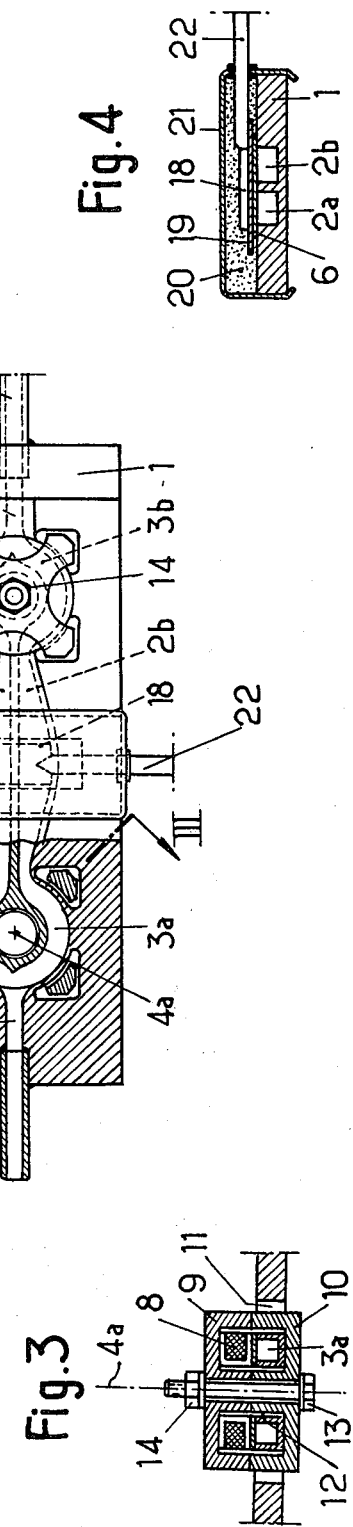

APPARATUS FOR MEASURING THE ELECTRICAL CONDUCTIVITY OF A LIQUID

FIELD OF THE INVENTION

The present invention relates to apparatus for measuring the electrical conductivity of a liquid.

The Prior Art

Apparatus is well known for measuring the electrical conductivity of a liquid which comprises an induction coil arranged to induce an alternating current in the liquid, and a measuring coil through which the alternating current flows and in which it induces an alternating voltage, the value of the latter constituting a measurement of the electrical conductivity of the liquid.

In particular, apparatus of this kind is known in which the liquid is divided between two parallel channels of the same electrical resistance, in the region of the induction coil and the measuring coil, in order to form a basically closed circuit for the electric current. In most forms of such apparatus, the induction coil is arranged in one of the channels and the measuring coil in the other. However, an external electrical circuit may be produced in the liquid, for example, if it is passed through the channels by means of a pump. Such an external circuit disturbs the resulting measurement so that the latter is therefore inaccurate.

In order to overcome this disadvantage, it has previously been proposed that an induction coil should be used (and, possibly also a measuring coil) in each of the channels, so that the same current is produced in both channels and the influences of the parasitic external circuit are therefore cancelled out. However, such an arrangement complicates the apparatus since it requires two induction coils and, in practice, two measuring coils. Moreover, it is necessary in practice to arrange the induction coil and the measuring coil around one another in each channel; consequently, an interaction takes place between the two coils which also serves to falsify the measurement.

Object of the Invention

It is an object of the present invention to provide an apparatus for measuring the electrical conductivity of a liquid, in which the liquid is divided between two parallel channels and which contains only a single induction coil and a single measuring coil, while still providing an accurate measured result.

SUMMARY OF THE INVENTION

According to the invention, apparatus for measuring the electrical conductivity of a liquid comprising two channels for the liquid connected in parallel, an induction coil and a measuring coil, a respective one of the two coils being located at each of the two points of connection of said two channels.

In such an apparatus, the influence of the parasitic external circuit is eliminated. In addition, the two coils, being arranged at the ends of two channels, are relatively far apart so that there is no direct interaction between them.

Preferably, at each of the two ends, the two channels are connected together by a circular passage above which the corresponding coil is arranged, the latter being coaxial with the circular passage.

DESCRIPTION OF DRAWING

The invention will now be further described with reference to the drawing, in which:

FIG. 1 is a side view of an apparatus according to the invention;

FIG. 2 is a view partly in section taken along the line II—II of FIG. 1;

FIG. 3 is a section taken along the line III—III of FIG. 2; and

FIG. 4 is a view taken along the line IV—IV of FIG. 1.

SPECIFIC DESCRIPTION

Referring to the drawing, the apparatus comprises a plate 1 in one face of which there are formed two substantially parallel passages 2a and 2b respectively connected with one another via circular passages 3a and 3b respectively having respective axes 4a and 4b and extended away from the parallel passages in the form of two passages 5a and 5b respectively. The plate 1 is provided with an elongated cover 6 which closes off the various passages and is attached to the plate, for example, by means of an adhesive; two pipes 7a and 7b are respectively connected to the passages 5a and 5b, these pipes being fixed between the plate 1 and the cover 6.

An induction coil 8 is arranged coaxially with the circular passage 3a above the plate 1 in a cross-shaped former 9. The former cooperates with a former 10 which is also cross-shaped and completes the magnetic circuit. The former 10 is arranged beneath the plate 1 and its arms extend into openings 11 in the plate 1 whilst its central part passes through an opening 12 in the plate along the axis 4a. The two formers 9 and 10 are fixed to one another by means of a bolt 13 and a nut 14.

In a similar fashion, a measuring coil 15 is arranged coaxially with the circular passage 3b in a second former 9 which cooperates with a second former 10 fixed to the second former 9 by means of a bolt 13 and a nut 14.

The two coils 8 and 15 are connected by respective conductors 16 and 17, respectively to an AC source and to a measuring instrument, the AC source and the instrument not being shown in the drawing.

In operation, the liquid whose electrical conductivity is to be measured is fed to the apparatus through the pipe 7a and is discharged through the pipe 7b, after having successively flowed through the passage 5a, the circular passage 3a, the parallel passages 2a and 2b, the circular passage 3b and the passage 5b. If, during passage of the liquid, an alternating current is supplied to the coil 8, then an electric current will be induced in the liquid and will flow in a closed loop via the passages 2a and 2b and the circular passages 3a and 3b. The current in turn induces in the coil 15 an alternating current, the voltage of which is a function of the conductivity of the liquid flowing through the apparatus and therefore represents a measure of this conductivity.

In order to enable any necessary correction of the measured value as a function of temperature to be made, a resistor 18 made, for example, of platinum, is placed astride the passages 2a and 2b, above the cover 6, an insulating plate 19 being interposed as shown in FIG. 4. This resistor is covered with a thermal insulator 20 held in position by a casing 21; its ends are connected by leads 22 to a correcting device which has not been shown.

It goes without saying that the present invention is not limited to the embodiment described and illustrated here but covers all the possible variant embodiments.

What I claim as my invention and desire to secure by Letters Patent of the United States is:

1. An apparatus for measuring the electrical conductivity of a liquid, comprising means having an inlet for said liquid, an outlet for said liquid and a pair of parallel channels independent from one another and interconnecting said inlet and said outlet; and an induction coil and a measuring coil, one of said coils being disposed at the junction of said channels with said inlet and the other of said coil being disposed at the junction of said channels with said outlet whereby said induction coil induces a current in said liquid through said channels and said measuring coil detects the current induced in said liquid at a location offset from said induction coil with respect to the direction of flow of said liquid from said inlet to said outlet.

2. The apparatus defined in claim 1 wherein said junctions are formed by respective passages extending along circular arcs, the respective coils being coaxial with said arcs.

3. The apparatus defined in claim 2 wherein said means forming said inlet, said outlet and said channels includes a plate provided with grooves constituting said inlet, said outlet and said channels, and a cover overlying said plate.

4. The apparatus defined in claim 3 wherein each of said coils includes a first former underlying said plate and having upwardly extending arms traversing same, a second former overlying said plate and having arms meeting the arms of said first former, said second former having a core, and a winding surrounding said core.

* * * * *